United States Patent [19]

Yeomans et al.

[11] Patent Number: 4,727,861

[45] Date of Patent: Mar. 1, 1988

[54] JOINT FOR ORTHOTIC DEVICE

[75] Inventors: Douglas Yeomans, Birmingham; Barry Martin, Tamworth, both of England

[73] Assignee: Weston Hydraulics Limited, Birmingham, England

[21] Appl. No.: 73,317

[22] Filed: Jul. 13, 1987

Related U.S. Application Data

[63] Continuation of Ser. No. 791,524, Oct. 25, 1985, abandoned.

[30] Foreign Application Priority Data

Dec. 6, 1984 [GB] United Kingdom ................. 8430832

[51] Int. Cl.⁴ .............................................. A61H 3/00
[52] U.S. Cl. .................................. 128/80 C; 128/83.5; 128/88; 623/39
[58] Field of Search ...................... 128/80 C, 88, 83.5, 128/84 R; 623/39, 43, 44

[56] References Cited

U.S. PATENT DOCUMENTS

| | | | |
|---|---|---|---|
| 1,477,070 | 12/1923 | Martin . | |
| 2,561,370 | 7/1951 | Henschke | 623/44 |
| 2,573,866 | 11/1951 | Murphy et al. . | |
| 2,632,440 | 3/1953 | Hauser et al. . | |
| 2,646,793 | 7/1953 | Swiech | 623/44 |
| 3,934,273 | 1/1976 | Mortensen | 623/44 |
| 3,982,279 | 9/1976 | Valenti | 623/44 |
| 4,005,496 | 2/1977 | Wilkes | 623/44 |
| 4,135,254 | 1/1979 | Weber | 623/43 |
| 4,310,932 | 1/1982 | Nader | 623/39 |
| 4,370,977 | 2/1983 | Mauldin | 128/88 |
| 4,397,308 | 8/1983 | Hepburn | 128/88 |
| 4,463,751 | 8/1984 | Bledsoe | 623/39 |
| 4,502,472 | 3/1985 | Pansiera . | |
| 4,554,913 | 11/1985 | Womack | 128/88 |
| 4,556,053 | 12/1985 | Irons | 128/88 |

FOREIGN PATENT DOCUMENTS

| | | | |
|---|---|---|---|
| 0016268 | of 0000 | European Pat. Off. . | |
| 0059472 | of 0000 | European Pat. Off. . | |
| 489216 | 1/1930 | Fed. Rep. of Germany | 623/39 |
| 2226686 | 10/1973 | Fed. Rep. of Germany | 623/44 |
| 1422891 | of 0000 | France . | |
| WO84/03433 | of 0000 | PCT Int'l Appl. . | |
| 358545 | of 0000 | Switzerland . | |
| 583799 | 12/1977 | U.S.S.R. | 128/80 C |

OTHER PUBLICATIONS

European Search Report-EP 79 300 423.5, Appln. No. 0016268.

Primary Examiner—Clyde I. Coughenour
Attorney, Agent, or Firm—Cushman, Darby & Cushman

[57] ABSTRACT

A joint for an orthotic device comprises a pair of pivotally connected members and means for limiting the angle through which the members may pivot, the limit means being adjustable so that the angle through which the members are permitted to move may be adjusted to a predetermined desired value, the joint has been found to be particularly suitable in a hip guidance orthosis.

14 Claims, 6 Drawing Figures

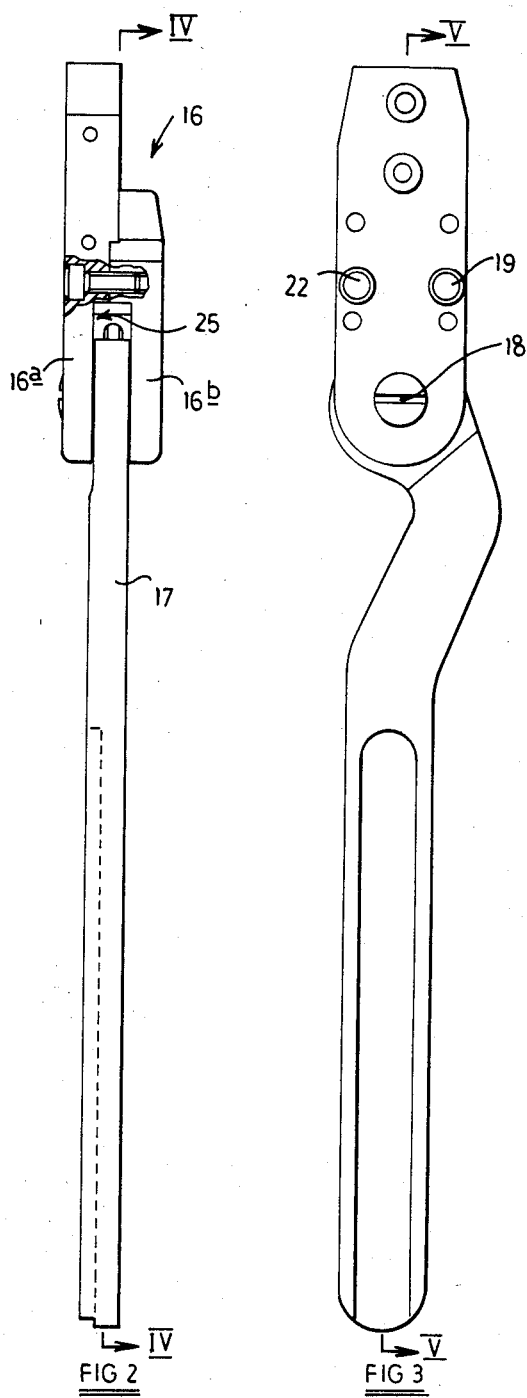

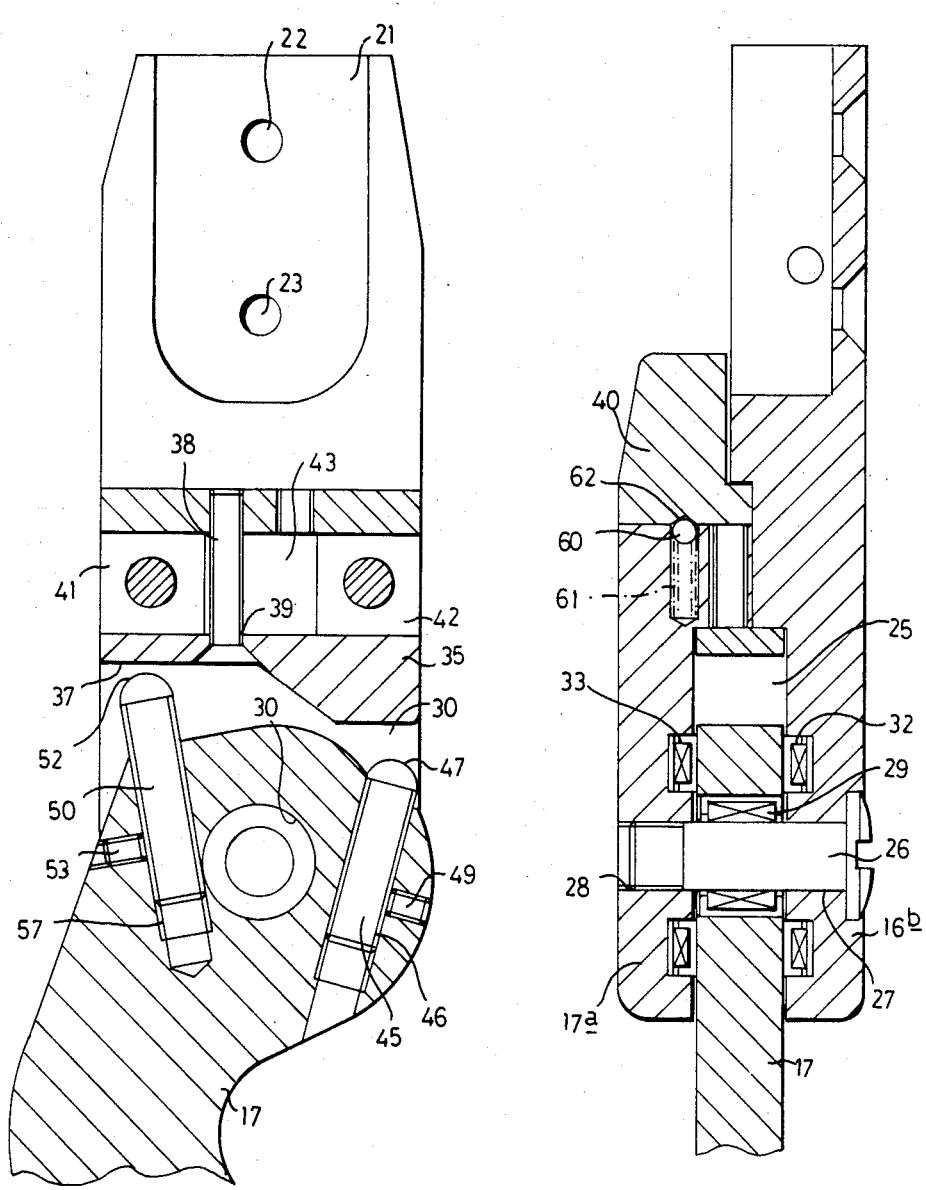

JOINT FOR ORTHOTIC DEVICE

This is a continuation of application Ser. No. 791,524, filed Oct. 25, 1985, which was abandoned upon the filing hereof.

BACKGROUND TO THE INVENTION

The present invention relates to a joint for an orthotic device and is primarily concerned with a joint for a "hip guidance orthosis", such an orthosis comprising a substantially rigid body brace to which is connected, via an articulated joint, leg calipers.

Hip guidance orthoses are known and are provided with adjustable fixing means whereby the body brace and leg calipers may be adjusted so as to be fitted to people of different sizes. The joint however, by means of which the leg calipers are mounted relative to the body brace, provides a problem since it is essential that only limited relative movement is provided and, both the amount and direction of permissible movement to enable a person walking with such a device to achieve satisfactory mobility, varies from person to person.

It is an object of the present invention to provide a new or improved joint for an orthotic device.

SUMMARY OF THE INVENTION

According to the present invention, we provide an orthotic device comprising:
1. a first member;
2. a second member;
3. a pivotal joint interconnecting said first and second members;
4. limit means to limit pivotal movement between said first member and said second member;
5. adjustment means to adjust the position of said limit means to limit the maximum angular movement of said first and said second members to a predetermined desired angle;
6. locking means operative to prevent undesired movement of said limit means.

Preferably means are provided to limit the pivotal movement in both pivotal directions from a predetermined relative angular position of said first and second members.

Preferably, said adjustment means for limiting said movement comprises pairs of abutting surfaces, one of each pair being provided on said first member and the other of each pair being provided on said second member.

Preferably, adjustment means is provided by adjustment parts provided on one of said members and affixed thereto, each of said adjustment parts providing one of the abutment surfaces of each pair, said adjustment parts being movable relative to the member to which they are affixed so as to provide said adjustment means, securing means being provided to prevent undesired relative movement between the adjustment parts and said member.

Preferably, said adjustment parts are threadedly engageable with one of said members and said securing means may comprise a further threaded member capable of movement into or out of engagement with said adjustment part.

Preferably, said adjustment parts are arranged so that when said abutment surfaces abut each other the adjustment parts and other members affording the abutment surfaces are subjected to minimal shearing forces.

Preferably, said joint includes further means whereby at least one of said abutment surfaces may be moved from a normal in-use position to permit of relative pivotal movement of said first and second members beyond at least one of the normal limiting positions.

Such a facility is of considerable benefit where the joint forms a movable "hip joint" in a hip guidance orthosis where it is required for the person wearing the orthosis to sit down, which requires a much greater angular movement between the body and the legs than is normal when walking.

Preferably, the other abutment surfaces of each pair are provided on an abutment part and conveniently said abutment part may be movably mounted on the member to which it is affixed from a first in-use position in which relative pivotal movement between said first and second members is limited by contact between said pairs of abutment surfaces, and a second position in which at least one of said surfaces provided on said abutment part is moved to a position to permit of considerably greater relative angular movement between said first and second members.

Preferably, said abutment part is slidably mounted on the member to which it is affixed, and conveniently, means are provided to retain the abutment part in either its in-use position or said other position.

Conveniently said retaining means may comprise a spring loaded member mounted in said abutment part, or the member to which it is affixed and extending into a recess provided in said member or said abutment part respectively.

Said first member may comprise an assembly of parts which conveniently define a fork or channel like arrangement, in which fork or channel is mounted the second member preferably through the intermediary of bearings.

Preferably, said joint comprises a part of a hip guidance orthosis and conveniently said first member is formed integrally with or is secured to a rigid body brace, and said second member is formed integrally with or connected to leg calipers.

Said second member, when forming part of or being attached to a leg caliper, is preferably, in the region of said pivotal connection, of C-like curved form to provide an open formation, which formation is particularly beneficial in providing the degree of movement required between said first member and said second member for movement beyond the normal limits to permit of a person wearing such hip guidance orthosis to take up a sitting position.

BRIEF DESCRIPTION OF THE DRAWINGS

The invention will now be described in more detail, by way of example only, with reference to the accompanying drawings, wherein:

FIG. 2 is a front view partly in section of one joint of the present invention;

FIG. 3 is a side elevation of the joint shown in FIG. 2;

FIG. 4 is a sectional view of the joint shown in FIG. 2 along the line 4—4;

FIG. 5 is a sectional view of the joint shown in FIG. 3 along the line 5—5; and

DESCRIPTION OF THE PREFERRED EMBODIMENTS

Figure 1:
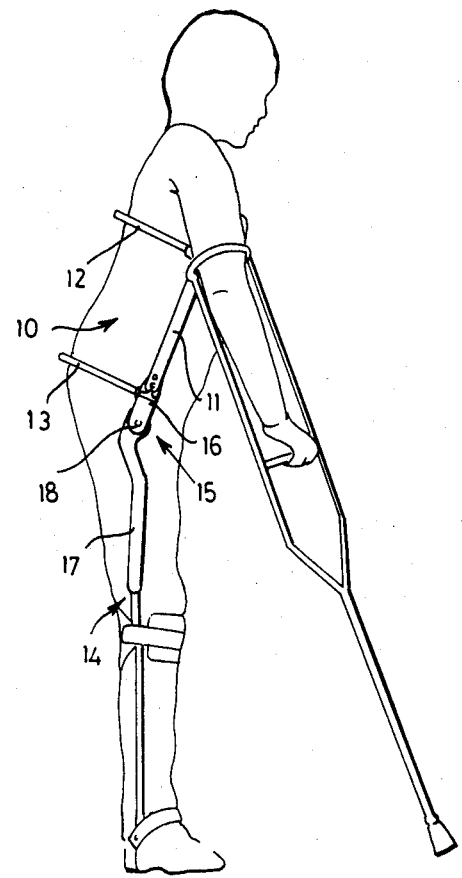
FIG. 1 is a diagrammatic view of a hip guidance orthosis using a joint of the present invention.

Referring first to FIG. 1, the hip guidance orthosis shown in the drawing comprises a rigid body brace generally indicated at 10 and comprising an upright member 11 rigidly affixed to the body by upper "strap" 12 and lower "strap" 13. A thoracic strap (not shown) across the chest of the user ensures that the body brace is firmly secured to the user.

The upright member 11 is connected to a leg caliper generally indicated at 14 through the intermediary of a joint generally indicated at 15.

The joint 15 includes a first member 16 which may either be formed integrally with the upright member 11 or secured thereto, and a second member 17 pivotally connected to the first member 16 about a pivotal axis 18, the second member 17 being connected to the leg caliper 14 or being formed integrally therewith.

The joint generally shown at 15 will now be described in more detail with reference to FIGS. 2 to 6.

The first member 16 comprises a first part 16a and a second part 16b secured to each other by threaded fasteners 19 and 20. The second part 16b is provided with a cut-out 21 and through bores 22 and 23 to enable securement of a rigid body brace 10.

The first and second parts 16a and 16b of the first member 16 define a channel 25 in which is pivotally mounted the second member 17 about pivotal axis 18.

The second member 17 is pivotally mounted within the channel 25 defined by the first member 16 by a threaded pivot pin 26 passing through bore 27 in the second part 16b and threadedly engaged with a thread form 28 provided on the first part 16a. A needle roller bearing 29 has an inner surface bearing on pivot pin 26 and an outer surface engaging a through bore 30 provided in second member 17.

A thrust bearing 32 is located between second part 16b and second member 17 and a similar thrust bearing 33 is located between first part 16a and second member 17.

A movable abutment part 35 and a forward abutment face 36 and a rearward abutment face 37. The abutment part 35 is slidably mounted relative to the first member 16 and secured thereto by means of a threaded member 38 passing through a through bore 39 in the abutment part and threadedly engaging a manually operable part 40.

Two spacer members 41 and 42 define a gap 43 therebetween permitting of limited movement of the manually operable member 40, together with abutment part 35.

Adjustment means are provided to limit relative pivotal movement about the axis 18 of the second member 17 relative to the first member 16. Means to limit forward, or anti-clockwise pivotal movement of the second member 17 relative to the first member 16 comprises a first adjustment part 45 threadedly engaged in a threaded bore 46 and providing an abutment face 47 which, in use, contacts the abutment face 36 on abutment part 35.

In view of the threaded engagement of the first adjustment part 45 relative to the second member 17 by rotating the adjustment part 45 about its longitudinal axis, it may be caused to extend further from the second member 17 or inserted further therein.

Locking means in the form of a grub screw 49 prevents undesired movement of the adjustment part 45 from a preset desired position.

A second adjustment part 50 is threadedly engaged within a threaded bore 51 and has an abutment face 52 adapted to make contact with the rearward abutment face 37 on abutment part 35 and is provided with a grub screw 53 to prevent undesired movement of the second adjustment part 50 from a preset desired position.

The provision of the adjustment parts 45 and 50 ensures that the angle of pivotal movement between the first member 16 and the second member 17 may be adjusted with a fine degree of accuracy and, from a predetermined angular relationship between the first member 16 and second member 17, the amount of movement in either pivotal direction may be adjusted independently of each other.

The abutment part 35 is shown in its in-use position in which the degree of pivotal movement between the first member 16 and second member 17 is limited to a predetermined amount.

Figure 6:
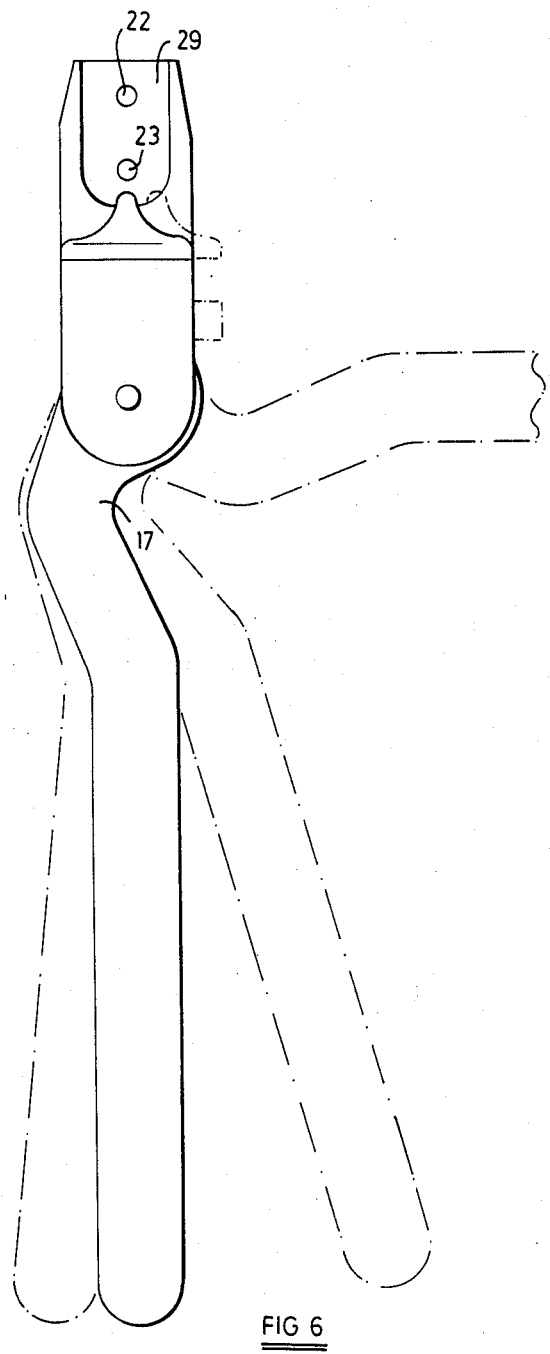
FIG. 6 is a side elevation of the joint, opposite to the side elevation shown in FIG. 3.

If the person to whom the device is fitted desires to sit down, then the manually operable member 40 is moved to the position shown in dotted outline in FIG. 6 and the forward abutment face 36 is moved to the position shown in dotted outline in FIG. 6, thus the abutment face 47 of first adjustment part 45 will not make contact with the abutment face 36 and a much greater angle of pivotal movement of the second member 17 in a clockwise direction relative to the first member 16 will be permitted, thus enabling the leg of a wearer of the apparatus to take up a position substantially at right angles to the body, i.e. a normal sitting position.

In order that undesired contact between the second member 17 and the first member 16 does not take place, the second member 17 is provided with a portion 54 of curved form and substantially of "open C-form", the "cut-out" in the C ensuring that the substantial angular movement necessary to enable a person to achieve a sitting position is possible.

Means are provided, in the form of a ball 60 urged by spring 61, to prevent undesired movement of the manually operable member 40 and hence the abutment part 35 from either its first in-use position, or its other position. The manually operable member 40 is provided with a pair of recesses, one of which may be seen at 62, in which the ball 60 is urged and hence the manually operable member 40, together with abutment part 35 is maintained in its desired position unless the manually operable member 40 is provided with sufficient force to cause the spring 61 to be depressed, permitting the ball 60 from disengaging from recess 62.

It will be appreciated that the force applied to the abutment part 35, in use of the apparatus, by contact with adjustment part 45 and 50 will be substantially at right angles to the force required to cause movement of the abutment part 35, thus ensuring that not only does undesired movement of the abutment part 35 not take place but, providing the force is applied in the right direction, only a small amount of force to move the abutment part 35 out of its in-use position to its other position is necessary.

The various parts of the joint as aforedescribed may be made of any suitable material, for example steel or if weight considerations are important, aluminium alloys or titanium or any other suitable alloy. It is further envisaged that some parts of the apparatus may be made from a plastics material which may be reinforced by other materials.

The joint as aforedescribed is only one preferred embodiment of the present invention and it is envisaged that alternative adjustment means may be provided and, furthermore, the joint of the present invention need not necessarily be provided with a hip joint in a hip guidance orthosis but may be provided in other orthotic devices.

The features disclosed in the foregoing description, in the following claims, or the accompanying drawings, expressed in their specific forms or in terms of a means for performing the disclosed function, or a method or process for attaining the disclosed result, or a class or group of substances or compositions, as appropriate, may, separately or in any combination of such features, be utilised for realising the invention in diverse forms thereof.

We claim:
1. An orthotic device comprising:
   a first member;
   a second member;
   a pivotal joint interconnecting said first and second members;
   an abutment member mounted on said first member and having first and second abutment surfaces;
   first limit means on said second member adapted to contact said first abutment surface to limit pivotal movement between said first member and said second member in a first pivotal direction;
   second limit means on said second member and adapted to contact said second abutment surface to limit pivotal movement between said first and said second members in a second pivotal direction opposite to said first pivotal direction;
   first and second adjustment means to adjust the position of said first and second limit means to limit the maximum angular movement of said first and said second members to a predetermined desired angle;
   first and second locking means operative to prevent undesired movement of said first and second limit means respectively;
   release means having an operating member operation of which moves said first abutment surface to a position out of range of contact with said first limit means to permit of relative movement of said first and second members beyond the limit position, provided by said first limit means.
2. A hip guidance orthotic device including a joint as claimed in claim 1.
3. An orthotic device as claimed in claim 1 wherein said first and second limit means comprises pairs of abutting surfaces, one of each pair being provided on said first member and the other of each pair being provided on said second member.
4. An orthotic device as claimed in claim 3 wherein said adjustment means comprises adjustment parts provided on one of said first and second members and affixed thereto, each of said adjustment parts providing one of the abutment surfaces of each pair, said adjustment parts being movable relative to the member to which they are affixed.
5. An orthotic device as claimed in claim 4 wherein said adjustment parts are threadedly engageable with one of said members.
6. An orthotic device as claimed in claim 4 wherein said adjustment parts are arranged so that when the surfaces of a pair of abutment surfaces abut each other said adjustment parts and the other members affording the abutment surfaces are subjected to minimal shearing forces.
7. An orthotic device as claimed in claim 1 wherein said securing means comprises a threaded member adapted for movement into or out of engagement with a respective adjustment part.
8. An orthotic device as claimed in claim 1 including means to override said limit means to enable said first and second members to be moved beyond its normal limited angular position.
9. An orthotic device as claimed in claim 8 wherein an abutment part is provided, which abutment part affords an abutment surface of at least one pair of said surfaces and wherein said abutment part is movably mounted onto said first or said second member.
10. An orthotic device as claimed in claim 9 wherein said abutment part is slidably mounted on one of said members and wherein retainment means are provided to remain said abutment part in either its in-use position in which it limits relative angular movement of said first and second members or a release position in which it permits of relative angular movement between said first and second members beyond said limited position.
11. An orthotic device as claimed in claim 10 wherein said retaining means comprises a spring loaded member mounted on said abutment part, or the member to which it is affixed, and extending into a recess provided in said member or said abutment part respectively.
12. An orthotic device as claimed in claim 1 wherein said first member comprises an assembly of parts which define a fork or channel like arrangement, in which fork or channel is pivotally mounted said second member.
13. An orthotic device as claimed in claim 1 wherein said joint comprises part of a hip guidance orthosis and wherein said first member is formed integrally with or is secured to a rigid body brace, and said second member is formed integrally with or connected to leg calipers.
14. An orthotic device as claimed in claim 1 wherein at least one of said first or second members is of curved form to provide an open C-like formation in the region of said pivotal connection.

* * * * *